(12) United States Patent
Ackerman et al.

(10) Patent No.: US 7,700,515 B2
(45) Date of Patent: Apr. 20, 2010

(54) AMORPHOUS SILICA-ALUMINA COMPOSITION AND METHOD OF MAKING AND USING SUCH COMPOSITION

(75) Inventors: Russell Craig Ackerman, Katy, TX (US); Christian Gabriel Michel, Houston, TX (US); John Anthony Smegal, Houston, TX (US); Johannes Anthonius Robert Van Veen, Cm Amsterdam (NL)

(73) Assignee: Shell Oil Company, Houston, TX (US)

( * ) Notice: Subject to any disclaimer, the term of this patent is extended or adjusted under 35 U.S.C. 154(b) by 0 days.

(21) Appl. No.: 12/197,391

(22) Filed: Aug. 25, 2008

(65) Prior Publication Data

US 2009/0062115 A1  Mar. 5, 2009

Related U.S. Application Data

(60) Provisional application No. 60/968,122, filed on Aug. 27, 2007.

(51) Int. Cl.
*B01J 21/00* (2006.01)
(52) U.S. Cl. .................. 502/263; 502/235; 502/234
(58) Field of Classification Search .................. None
See application file for complete search history.

(56) References Cited

U.S. PATENT DOCUMENTS

| | | | |
|---|---|---|---|
| 3,637,484 A | 1/1972 | Hansford | 208/143 |
| 3,943,053 A | 3/1976 | Kovach et al. | 208/143 |
| 4,289,653 A | 9/1981 | Jaffe | 252/453 |
| 4,499,197 A | 2/1985 | Seese et al. | 502/65 |
| 4,721,696 A * | 1/1988 | Kidd | 502/210 |
| 4,758,330 A | 7/1988 | Kidd | 208/213 |
| 4,780,446 A * | 10/1988 | Nozemack et al. | 502/235 |
| 4,849,093 A | 7/1989 | Vauk et al. | 208/143 |
| 4,988,659 A | 1/1991 | Pecoraro | 502/235 |
| 5,225,383 A | 7/1993 | Kukes et al. | 502/66 |
| 5,308,814 A | 5/1994 | Kukes et al. | 502/66 |
| 6,296,759 B1 | 10/2001 | Vaarkamp et al. | 208/217 |

(Continued)

FOREIGN PATENT DOCUMENTS

WO   WO9410263   5/1994

(Continued)

OTHER PUBLICATIONS

Ryoji Takahashi et al., "Silica-Alumina Catalyst with Bimodal Pore Structure Prepared by Phase Separation in Sol-Gel Process," *Journal of Catalysis*, 2001, pp. 197-202, XP002535065.

(Continued)

*Primary Examiner*—Melvin C Mayes
*Assistant Examiner*—Smita Patel
(74) *Attorney, Agent, or Firm*—Charles W. Stewart (57) ABSTRACT

Described is a novel amorphous silica-alumina composition having a high ratio of pore volume contained in large pores to pore volume contained in medium to small pores. The amorphous silica-alumina composition also may have the characteristic of a strong aluminum-NMR penta-coordinated peak representing greater than 30% of the total aluminum and a method of making such novel amorphous silica-alumina composition using a pH swing preparation method.

18 Claims, 3 Drawing Sheets

U.S. PATENT DOCUMENTS

| | | | |
|---|---|---|---|
| 6,872,685 B2 * | 3/2005 | Timken | 502/263 |
| 6,995,112 B2 | 2/2006 | Timken et al. | 502/240 |
| 2004/0065587 A1 | 4/2004 | Collin et al. | 208/89 |

FOREIGN PATENT DOCUMENTS

| WO | WO2005046855 | 5/2005 |
|---|---|---|

OTHER PUBLICATIONS

Shin-Ichi Inoue et al., "A New Concept for Catalysts of Asphaltene Conversion," Catalysis Today 43 (1998) pp. 225-232, XP002535066.

E. Lopez-Salinas et al., "Alumina NanoFibers Obtained by pH-Swing Method," 18$^{th}$ NAM Meeting, No. PRE-89, June 4, 2003, pp. 1-2, XP002535067.

* cited by examiner

AMORPHOUS SILICA-ALUMINA COMPOSITION AND METHOD OF MAKING AND USING SUCH COMPOSITION

This application claims the benefit of U.S. Provisional Application Ser. No. 60/968,122, filed Aug. 27, 2007.

The present invention relates to an amorphous silica-alumina composition and a method of making such composition.

The prior art presents numerous methods of manufacturing amorphous silica-alumina and it is recognized that the physical and catalytic properties of amorphous silica-alumina can be highly dependent upon the method by which it is manufactured. For example, U.S. Pat. No. 4,289,653 teaches that the properties of silica-alumina are highly dependent upon the manner by which it is manufactured, and it discloses one method of preparing silica-alumina compositions. The method disclosed includes the preparation of silica-alumina by mixing an alkali metal silicate (e.g. sodium silicate) with an aluminum salt (e.g. aluminum sulfate) and a mineral acid to form an acidified sol. A basic precipitant such as ammonium hydroxide is then added to the acidified sol to raise its pH and to thereby cause the cogelling of the silica and alumina species. The resulting cogelled mass of silica-alumina hydrogel is recovered from the solution and used in the preparation of denitrification and other hydroprocessing catalysts containing Group VI and Group VIII metals.

U.S. Pat. No. 4,499,197 teaches another method of making a silica-alumina composition. This patent teaches the manufacture of silica-alumina cogel by reacting an alkali metal aluminate (sodium aluminate) solution with an alkaline metal silicate (sodium silicate) solution to obtain a pregel silica-alumina reaction mixture having a pH of from 12 to 12.5. The pregel is then mixed with an aluminum salt (aluminum sulfate) and acidic rare earth solution, and, after aging, the resulting cogel is recovered. The amorphous silica-alumina cogels of the '197 patent may have a silica content of from 10 to 90 weight percent and an alumina content of from 10 to 90 weight percent. The cogels are characterized as having a surface area of from 100 to 400 m2/gm with from about 30 to 60 percent of its surface area that is contained in the pores having a diameter of from about 40 to 100 angstroms.

U.S. Pat. No. 4,988,659 discloses a silica-alumina cogel and a method of making such cogel. The cogel is made by adding a silicate solution to an aqueous solution of an acid and acid aluminum salt, such as aluminum chloride or aluminum sulfate, to form an acidified silica sol having a pH in the range of from 1 to 4 followed by raising the pH of the sol by adding a base, aging the sol, and recovering the resulting cogel. The recovered cogel can further be processed by use of an acid to induce syneresis, washing, and, then, spray drying. The final dried cogel has uses as a cracking catalyst, a support for hydrocracking applications and other uses.

U.S. Pat. No. 6,872,685 discloses an amorphous silica-alumina composition having a surface-to-bulk Si/Al ratio (SB ratio) that is in the range of from 0.7 to 1.3 and having less than 10% crystalline alumina phase present in the composition. The amorphous silica-alumina is prepared by mixing a silicate (sodium silicate) solution and an acid aluminum salt (aluminum sulfate) solution while maintaining the pH of the mixed solution at less than 3 followed by the gradual addition of a basic precipitant to the mixed solution to produce a precipitated cogel that can be recovered, washed and spray-dried. The cogel material may be used to produce a silica-alumina catalyst or catalyst support.

U.S. Pat. No. 6,872,685 teaches the use in numerous hydroconversion processing applications of compositions including amorphous silica-alumina that is made, in general, by the preparation of a sol containing silica and alumina followed by gellation of the sol. The cogel may be used as a catalyst support material or it may be combined with other components in matrices. The cogel has uses in hydrocracking, dewaxing, and hydrofinishing.

It is desirable to have an amorphous silica-alumina composition that has certain physical and catalytic properties making it especially useful as a catalyst or a component of a catalyst for use in various hydroprocessing applications.

It is also desirable to have a process for the preparation of amorphous silica-alumina having certain desired physical and catalytic properties.

It is further desirable to have a reasonably simple and economical process for the manufacture of amorphous silica-alumina compositions, and, in particular, amorphous silica-alumina compositions having certain desired physical and catalytic properties.

Accordingly, provided is a novel silica-alumina composition that comprises an amorphous silica-alumina having an A/B ratio (as hereinafter defined) exceeding 2.2. This silica-alumina composition can be made by combining within a mixing zone water and aluminum sulfate to provide a mixture having a pH in the range of from 1.5 to 6.5; thereafter, increasing the pH of said mixture to within the range of from 7.5 to 12 by adding sodium silicate to said mixture within said mixing zone; and recovering a precipitate solid from said mixture in said mixing zone, wherein said precipitate solid comprises said silica-alumina composition.

In another embodiment of the inventive method, a silica-alumina composition is made by forming within a mixing zone a precipitate solid comprising silica-alumina by: (a) introducing water into said mixing zone; (b) introducing aluminum sulfate into said mixing zone so as to provide a mixture comprising water and aluminum sulfate having a pH in the range of from 1.5 to 6.5; (c) thereafter, introducing sodium aluminate into said mixing zone to thereby increase the pH of said mixture to within the range of from 7.5 to 12; (d) thereafter, introducing aluminum sulfate into said mixing zone to thereby lower the pH of said mixture to within the range of from 1.5 to 6.5; and (e) thereafter, introducing sodium silicate into said mixing zone to thereby increase the pH of said mixture to within the range of from 7.5 to 12; and recovering said precipitate solid from said mixture.

In yet another embodiment of the inventive method, an amorphous silica-alumina composition is made by (a) combining water and aluminum sulfate to provide a first mixture having a pH in the range of from 1.5 to 6.5; (b) adding sodium aluminate to said first mixture to provide a second mixture having a pH in the range of from 7.5 to 12; (c) adding aluminum sulfate to said second mixture to provide a third mixture having a pH in the range of from 1.5 to 6.5; (d) adding sodium silicate to said third mixture to provide a forth mixture having a pH in the range of from 7.5 to 12; (e) adding aluminum sulfate to said forth mixture to provide a fifth mixture having a pH in the range of from 1.5 to 6.5; (f) adding sodium aluminate to said fifth mixture to provide a sixth mixture having a pH in the range of from 7.5 to 12; (g) adding aluminum sulfate to said sixth mixture to provide a seventh mixture having a pH in the range of from 1.5 to 6.5; (h) adding sodium silicate to said seventh mixture to provide an eighth mixture having a pH in the range of from 7.5 to 12; and (i) recovering a precipitate solid from said eight mixture, wherein said precipitate solid comprises said amorphous silica-alumina composition.

The inventive amorphous silica-alumina (ASA) composition has certain unique physical and catalytic properties that make it particularly suitable for use either alone as a catalyst or as a component of a composited catalyst. The inventive process for making the amorphous silica-alumina is a relatively simple and economical approach to making amorphous silica-alumina having certain unique physical and catalytic properties, and it utilizes a so-called pH swing manufacturing methodology to provide the amorphous silica-alumina composition of the invention with its unique properties.

The inventive process includes the preparation of a mixture that contains water, an aluminum salt and a silicate, and the ultimate formation of a precipitate solid by the sequential addition to or mixing with the mixture in one or more series or swings of an aluminum salt source that provides for a low or reduced mixture pH followed by the addition to or mixing with the mixture of either sodium aluminate or sodium silicate that provides for a high or increased mixture pH. This use of one or more pH swings in the formation of the silica-alumina precipitate is an essential feature of the inventive process.

What is meant by the use herein of the term "pH swing" is that the pH of the preparation mixture is changed or cycled from a low, acidic pH to a high, alkaline pH by the addition to the preparation mixture of an aluminum salt component in order to lower the pH to the acidic range of less than 7 followed by the addition to the preparation mixture of either sodium aluminate or sodium silicate in order to raise the pH to the basic range of greater than 7. After one or more pH swings, the resulting precipitate solid that is formed in the preparation mixture is recovered therefrom. It is believed that the use of this pH swing method of preparation provides for the novel amorphous silica-alumina composition of the invention with its unique physical and catalytic properties.

One of the advantageous features of the inventive pH swing process is that it allows for the use of a single vessel that defines a mixing or reaction zone for carrying out the mixing and precipitation reaction of the process. It is noted that in many of the prior art processes for making silica-alumina, multiple processing tanks are required for conducting various steps of the processes, such as, for example, a gelling step may be carried out in a different vessel from one that is used to prepare a silica sol, and different vessels may also be used in carrying out certain of the other steps of the prior art processes. The inventive process, on the other hand, provides for the use of a single mixing or reaction zone into which the components of the preparation mixture of the inventive process are added. This eliminates some of the manufacturing complexity that is often associated with the prior art silica-alumina manufacturing processes that require the use of multiple mixing, reaction and transfer tanks or vessels.

Another of the advantages of the inventive pH swing process is that it can significantly reduce the total preparation and precipitation time required for making the final slurry from which is recovered the precipitate solid that comprises the amorphous silica-alumina of the inventive process. The elapsed time for adding to the preparation mixture the components for each of the steps of the one or more pH swings can be minimized to provide for a short total precipitation time for the preparation of the final slurry that includes the precipitate solid. In many cases, the elapsed time for preparation of a final slurry can be significantly shorter than those of prior art processes.

In general, the inventive method includes, initially, combining water and aluminum sulfate in such amounts as to provide a mixture that has a pH that is acidic, i.e., a pH of less than 7. It is desirable for the pH of this initial mixture to be in the range of from 1.5 to 6.5, and, preferably, from 2 to 6. Most preferably, the initial mixture should have a pH that is in the range of from 2.5 to 5.5, and, especially preferred, from 3.1 to 5.1. Once this initial mixture is formed, the next step of the method includes adding an amount of either sodium aluminate or sodium silicate to the initial mixture in such an amount as to increase the pH of the resulting mixture so that it is alkaline, i.e. a pH of greater than 7. It is desirable for this pH to be in the range of from 7.5 to 12, and, preferably, from 8 to 11.5. Most preferably, the pH is in the range of from 8.5 to 11. These two process steps, which include a change in the mixture pH after the addition of the aluminum sulfate to lower the pH of the mixture followed by the separate addition of either the sodium aluminate or sodium silicate to increase the pH of the mixture, are, together, considered herein to be one pH swing. The time elapsed between the two addition steps of the pH swing method does not need to be large, but it only needs to be sufficiently long so as to allow for the substantial mixing of the added components. In the case where the components are combined together within a single mixing zone, it is desirable for the mixing time to be sufficient to allow for mixing of the components to provide a substantially homogeneous preparation mixture. An important feature of the inventive method is in the application of multiple pH swings in the preparation of the preparation mixture that becomes the final slurry of silica and alumina cogel, or, otherwise, a slurry of a precipitate solid comprising silica-alumina.

In a more specific embodiment of the inventive method, the components of the preparation mixture are combined together within a single mixing or reaction vessel that defines a mixing or reaction zone and which provides means for mixing or reacting the components so as to ultimately form a slurry of the precipitate solid that comprises the silica-alumina of the invention. The mixing or reaction vessel can be any suitable vessel and associated equipment known to those skilled in the art including a vessel that is equipped with means for stirring the contents of the vessel, such as a rotating impeller, to provide for blending and dispersing of the components therein and suspending and dispersing of precipitate solids of the preparation mixture of the inventive method. The vessel may also be operatively equipped with means for exchanging heat with the contents of the vessel in order to provide for the control of the temperature of the vessel contents.

In this embodiment of the inventive process, which utilizes a single mixing zone, water and aluminum sulfate are first introduced into the mixing zone in such amounts and proportions so as to provide a mixture that comprises water and aluminum sulfate having a pH that is in the range of from 1.5 to 6.5, preferably, from 2 to 6, and, most preferably, from 2.5 to 5.5, and, especially, from 3.1 to 5.1. After the mixing of the water and aluminum sulfate is completed, sodium aluminate is then introduced into the mixing zone and mixed with the mixture therein in an amount so as to increase the pH of the mixture to within the range of from 7.5 to 12, preferably, from 8 to 11.5, and, most preferably, from 8.5 to 11.

It is desirable to minimize the time required for mixing the components of each addition step of the method to only that which is required to provide a homogenous mixture within the mixing zone. While the mixing time can vary depending upon the type of equipment utilized, the equipment size, and other factors, the time required to combine, blend and disperse the components should, generally, be in the range of from 1 to 30 minutes per addition step.

After the completion of the aforedescribed pH swing, aluminum sulfate is again introduced into the mixing zone and mixed with the preparation mixture contained therein in an amount so as to lower its pH to within the range of from 1.5 to 6.5, preferably, from 2 to 6, most preferably, from 2.5 to 5.5, and, especially preferred, 3.1 to 5.1. This step is followed by the introduction of sodium silicate into the mixing zone and mixing it with the preparation mixture therein in an amount so as to increase the pH of the mixture to within the range of from 7.5 to 12, preferably, from 8 to 11.5, and, most preferably, from 8.5 to 11, which completes the second pH swing.

The formed precipitate solids contained in the preparation mixture after the completion of the second pH swing may be recovered from the remaining liquid, which sometimes is referred to as the mother liquor, by any of the methods known to those skilled in the art; however, it is preferred to continue with the sequence of pH swings before recovering the precipitate solids that are formed in the final slurry of the preparation mixture of the inventive process.

Thus, after the completion of the second pH swing, aluminum sulfate is again introduced into the mixing zone and mixed with the mixture therein in an amount so as to lower the pH of the mixture to within the range of from 1.5 to 6.5, preferably, from 2 to 6, most preferably, from 2.5 to 5.5, and, especially preferred, from 3.1 to 5.1. This step is followed by the introduction of sodium aluminate into the mixing zone and mixing it with the preparation mixture therein in an amount so as to increase the pH of the preparation mixture to within the range of from 7.5 to 12, preferably, from 8 to 11.5, and, most preferably, from 8.5 to 11, to complete the third pH swing.

Following the completion of the third pH swing, aluminum sulfate is again introduced into the mixing zone and mixed with the preparation mixture therein in an amount so as to lower the pH of the preparation mixture to within the range of from 1.5 to 6.5, preferably, from 2 to 6, most preferably, from 2.5 to 5.5, and, especially preferred, from 3.1 to 5.1. This step is followed by the introduction of sodium silicate into the mixing zone and mixing it with the preparation mixture therein in an amount so as to increase the pH of the preparation mixture to within the range of from 7.5 to 12, preferably, from 8 to 11.5, and, most preferably, from 8.5 to 11, to complete the fourth pH swing. Upon the completion of the fourth pH swing, the formed precipitate solids contained in the final slurry of the preparation mixture are recovered from the remaining liquid.

The temperature conditions at which the preparation mixture is formed within the mixing zone of the inventive process can affect the properties of its amorphous silica-alumina end-product with higher preparation temperatures tending to yield material that is more crystalline and lower preparation temperatures tending yield material that is more amorphous. However, there can be limits on the temperature conditions required for yielding a desired product. Thus, it is desirable to control the mixing and reaction temperatures of the process steps to within certain defined temperature ranges. Generally, the mixing and reaction temperatures of each of the pH swings should be in the range of from 20° C. to 90° C., preferably, from 30° C. to 80° C., and, most preferably, from 40° C. to 70° C. It is especially desirable for the mixing and reaction of the components to take place in as close to isothermal conditions as is feasible with the use of typical commercial mixing and reaction process equipment. In addition to the control of the mixture pH of the various addition steps of each of the pH swings, it is also desirable to combine the components in amounts such as to provide a final slurry mixture from which the precipitate solids are recovered that has a solids content of from 1 to 30 weight percent (wt. %), based upon the total weight of the preparation mixture. Preferably, the proportion of solids in the final slurry mixture is in the range of from 2 to 20 wt. %, and, most preferably, from 3 to 15 wt. %.

To provide for the desired weight percentage of precipitate solids in the final slurry of the inventive process the relative amounts of the aluminum sulfate, sodium aluminate and sodium silicate for each of the pH swings are adjusted within certain desired ranges. For example, in the pH swings that involve the addition of aluminum sulfate followed by the addition of sodium aluminate, the weight ratio of the sodium aluminate-to-aluminum sulfate for the components added to the preparation mixture should, generally, be in the range of from 0.1 to 1.5, but, preferably, from 0.3 to 1.1, and, most preferably, from 0.5 to 0.9. In the pH swings that involve the addition of aluminum sulfate followed by the addition of sodium silicate, the weight ratio of the sodium silicate-to-aluminum sulfate should, generally, be in the range of from 0.5 to 5, but, preferably, from 1 to 4, and, most preferably, from 1.5 to 3.

The form in which the aluminum sulfate, sodium aluminate and sodium silicate is added to the preparation mixture of the inventive process may be either as a dry solid or as an aqueous solution of the particular component.

Any suitable method known to those skilled in the art for separating the precipitate solids from the remaining fluid of the final slurry or preparation mixture may be used to recover the precipitate solid. Such methods include gravity separation, pressure separation, and vacuum separation and can include the use of equipment such as, for example, belt filters, plate-and-frame filters and rotary vacuum filters.

The filtered precipitate solids, or filter cake, may be washed with water to remove impurities such as sodium and sulfate salts. The amount of water used to wash the precipitate solids may be any amount that suitably provides a washed powder having a pH that is within the desirable range of from 2 to 7, and, preferably, from 2.5 to 5.5. The weight ratio of water to dry powder used in a single washing step can be in the range of from 0.1:1 to 100:1, preferably, from 0.5:1 to 50:1. One or more washing steps may be used to wash the filtered precipitate solids. The washed precipitate may also be reslurried and spray-dried using any of the suitable spray-drying methods known to those skilled in the art to provide a spray-dried powder.

The spray-dried powder may further be processed by drying or calcination, or both, or it, or the dried and/or calcined powder, may be composited with other components to form a composited composition. The spray-dried powder may be dried in air or any other suitable atmosphere under otherwise suitable drying conditions at a drying temperature in the range of from 50° C. to 200° C., preferably, from 60° C. to 180° C. The spray-dried powder, preferably after further being dried, may be calcined under suitable calcination conditions, and, in particular, in an oxygen-containing atmosphere, such as, for example, air, at a calcination temperature in the range of from 275° C. to 1000° C., preferably, from 300° C. to 800° C., and, most preferably, from 350° C. to 600° C. The inventive amorphous silica-alumina, either alone or when composited with other components to form a composited catalyst composition, can be useful in a wide variety of hydrocarbon processes, including, for example, hydrocracking, hydrotreating (e.g. hydrodesulfurization, hydrodenitrogenation, and hydrodemetallization), hydrofinishing, isomerization, polymerization, catalytic dewaxing, and catalytic cracking. Possible feedstocks that can be processed or treated using the inventive amorphous silica-alumina include hydrocarbons that boil in the gasoline boiling range, distillate hydrocarbons, including diesel and kerosene, gas oils, including atmospheric gas oil and vacuum gas oil, atmospheric or vacuum residues, deasphalted oils, catalytically cracked cycle oils, coker gas oils and other thermally cracked gas oils and syncrudes.

The recovered precipitate is a unique silica-alumina composition that is highly amorphous in that it contains very little alumina that is crystalline. The amount of crystalline alumina in the silica-alumina composition is indicated by its characteristic powder X-ray diffraction (XRD) pattern that has a significant lack of XRD peaks which are representative of various of the crystalline alumina phases. Generally, the amount of alumina that is in the crystalline phase contained in the amorphous silica-alumina is less than 10 weight percent of the total weight of the silica-alumina composition. More specifically, the amorphous silica-alumina composition has less than 8 weight percent crystalline alumina, and, most specifically, it has less than 5 weight percent crystalline alumina.

The amorphous silica-alumina composition can have a silica content that is in the range of from 10 to 90 weight percent, with the weight percent being based on the total dry weight of the silica-alumina composition. The preferred silica content, however, is in the range of from 25 to 75 weight percent, and, most preferred, the silica content is in the range of from 40 to 60 weight percent. The alumina may be present in the silica-alumina composition in an amount in the range of from 10 to 90 weight percent, more specifically, from 25 to 75 weight percent, and, most specifically, from 40 to 60 weight percent.

One advantageous property of the amorphous silica-alumina composition is that it has a relatively high ratio of its pore volume that is contained in its large pores to its pore volume that is contained in its medium and small pores. One measure of this property is the ratio of the pore volume (cc/gm) contained in the pores of the amorphous silica-alumina composition having a pore diameter of less than 2150 Å ("A") to the pore volume contained in the pores of the amorphous silica-alumina composition having a pore diameter of less than 210 Å ("B"). This ratio of A-to-B (A/B), in general, should exceed 2.2, and, preferably, the A/B ratio exceeds 2.4, and, most preferably, the A/B ratio exceeds 2.5.

References herein to total pore volume are to the pore volume as determined using the Standard Test Method for Determining Pore Volume Distribution of Catalysts by Mercury Intrusion Porosimetry, ASTM D 4284-88, at a maximum pressure of 4000 bar, assuming a surface tension for mercury of 484 dyne/cm and a contact angle with amorphous silica-alumina of 140°.

Another characteristic of the amorphous silica-alumina composition is that it has a significantly high surface area and total pore volume. Its surface area can be in the range of from 190 m2/gm to 400 m2/gm, but, more specifically, it is in the range of from 200 m2/gm to 350 m2/gm, and, more specifically, from 225 m2/gm to 325 m2/gm. The total pore volume of the amorphous silica-alumina composition is in the range of from 0.8 cc/gm to 1.3 cc/gm, more specifically, from 0.9 cc/gm to 1.2 cc/gm, and, most specifically, from 0.95 cc/gm to 1.1 cc/gm.

The amorphous silica-alumina composition of the invention is further characterized by its Aluminum (27Al) solid-state NMR spectrum. The aluminum solid-state NMR spectrum of the amorphous silica-alumina composition has three significant peaks: a first peak located at about 65 ppm on the chemical shift scale representing tetrahedral aluminum sites; a second peak located at about 30 ppm on the chemical shift scale representing penta-coordination aluminum sites; and a third peak located at about 3 ppm on the chemical shift scale representing octahedral aluminum sites. These chemical shifts are referenced to aqueous aluminum chloride at 0.0 ppm. The shifts of the aforementioned peaks can be influenced by the acidity and second order quadrupolar interaction experienced by the respective aluminum nuclei.

Figure 1:
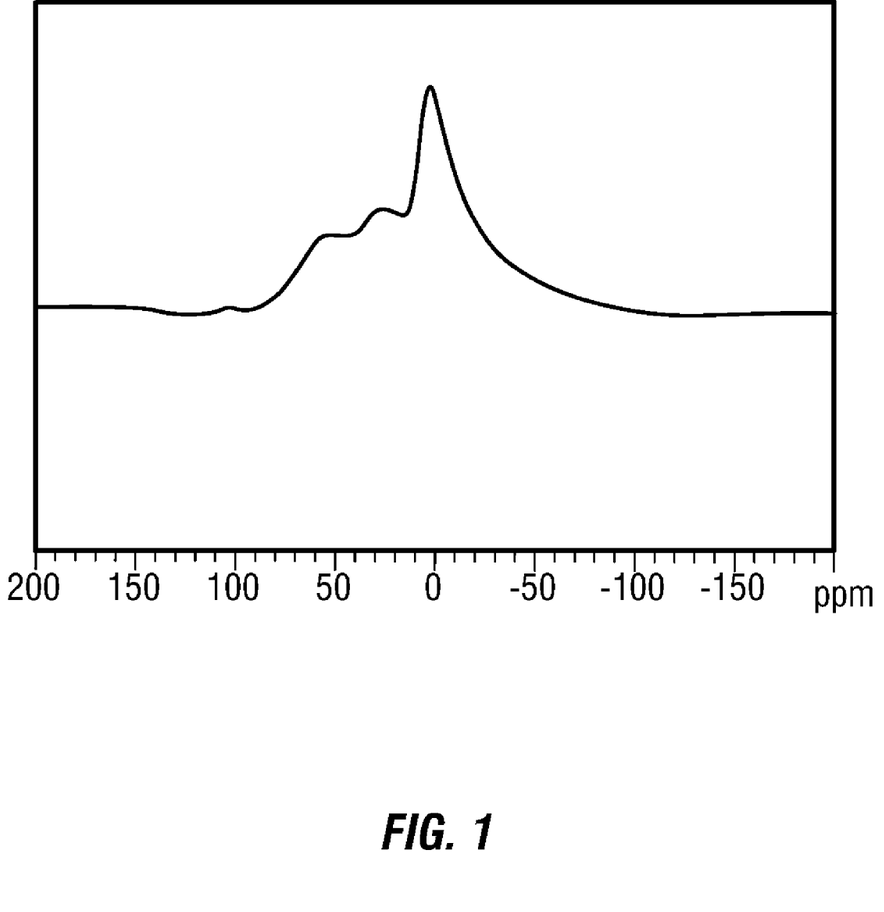
FIG. 1 presents the aluminum ($^{27}$Al) solid-state NMR spectrum of the inventive amorphous silica-alumina powder.

FIG. 1 presents a representative 27Al solid-state NMR spectrum for the inventive amorphous silica-alumina. One important characteristic of this spectrum is that it includes a strong penta-coordination peak, which represents the presence of penta-coordinated aluminum (Al). The penta-coordination peak and its strength are an indication of the disorder of and defects in the structure of the inventive amorphous silica-alumina, and it is believed that the penta-coordinated aluminum contained in the inventive amorphous silica-alumina composition adds to its acidity thereby providing for enhanced catalytic activity when used in catalyst applications. Generally, the penta-coordination peak should have a relative size to the other aluminum peaks so as to represent the presence of penta-coordinated aluminum in an amount greater than 30 percent of the total of the three types of aluminum represented by the three peaks of the NMR spectrum. More specifically, the strong penta-coordination peak of 27Al solid-state NMR spectrum of the amorphous silica-alumina should be greater than 35% of the total of the three types of aluminum, and, most specifically, it should be greater than 40% of the total of the three types of aluminum.

As referenced herein, the NMR spectrum of the amorphous silica-alumina composition is that which is generated using any standard Solid-State Nuclear Magnetic Resonance (NMR) spectroscopy methodology known to those skilled in the art of using NMR techniques for characterizing structural configurations of solid materials. The determination of the NMR spectrum of the amorphous silica-alumina composition can be made by using any suitable instrumentation and equipment that provide a spectrum that is substantially similar to one which can be provided by using the NMR spectrometer manufactured and marketed by Varian, Inc of Palo Alto, Calif. as Varian 400-MR NMR spectrometer using a Doty Scientific, Inc. of Columbia, S.C., 5 mm high power solid-state NMR probe. Samples are loaded into a 5 mm silicon nitride (Si3N4) rotor and spun at 13 to 16 kHz (780,000 to 960,000 rpm) in a dry nitrogen atmosphere at room temperature. The stator housing is adjusted to be at a magic angle to the external magnetic field to minimize the broadening caused by random orientation of the individual nuclei with reference to the external magnetic field. The resonance frequency for aluminum nuclei at this field strength is 104.3 MHz. The spectral width of 0.5 MHz, a pulse width of 1.0 microsecond, and a recycle delay of 0.3 seconds are employed as the experimental conditions.

Figure 2:
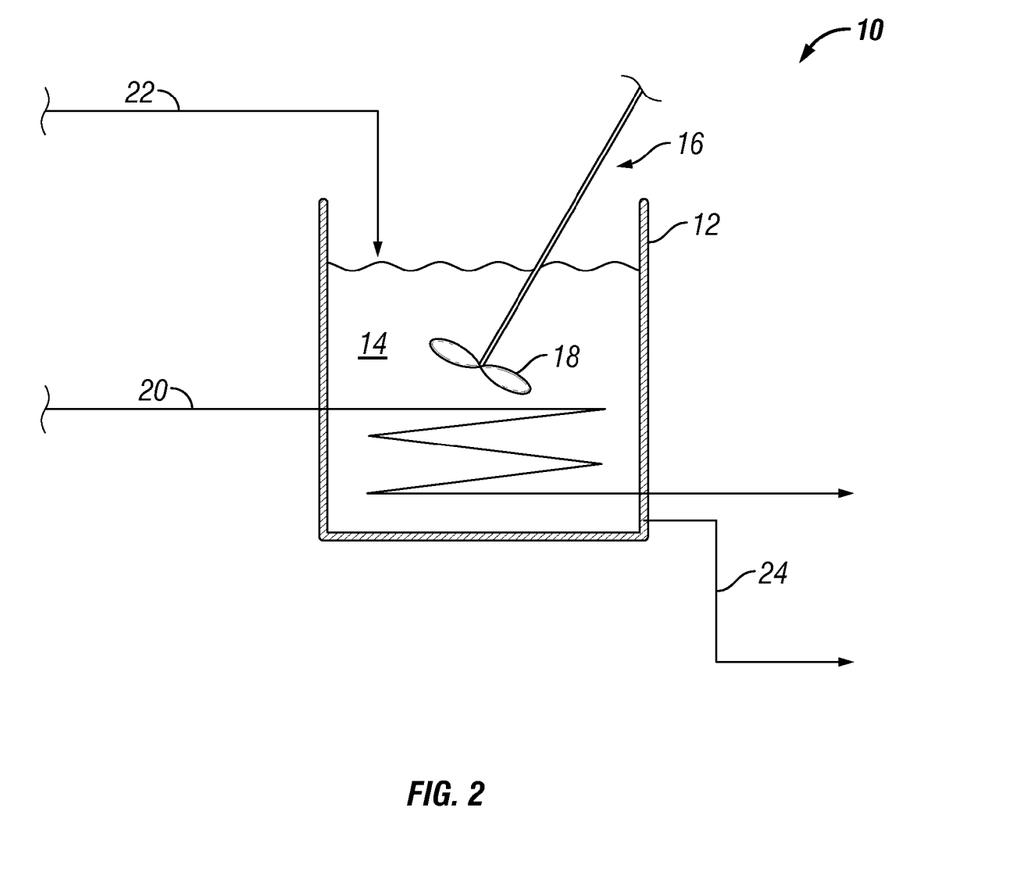
FIG. 2 is a schematic that depicts certain aspects of the inventive method and associated equipment used to manufacture the inventive amorphous silica-alumina composition.

One embodiment of the inventive pH swing method of making a silica-alumina composition includes four pH swings and is now described with reference to FIG. 2. Shown in FIG. 2 is an equipment system 10 that provides for the application of the pH swing method for making an amorphous silica-alumina product having certain unique physical properties including having a high macroporosity and exhibiting a characteristically strong aluminum-NMR penta-coordination peak representing greater than 30% of the total aluminum of the composition. The equipment system 10 includes a mixing or reaction vessel 12, which defines a mixing or reaction zone and provides means for mixing or reacting the components of the preparation mixture 14 contained within the mixing or reaction vessel 12.

The mixing or reaction vessel 12 is, preferably, equipped with a stirring device 16, that may include a rotating impeller 18 that provides means for blending and dispersing of the components of preparation mixture 14. The mixing or reaction vessel 12 may also be operatively equipped with a heat transfer coil or heat transfer jacket 20, which provides means for exchanging heat with the preparation mixture 14 of the mixing or reaction vessel 12 in order to provide for the control of its temperature.

In the first pH swing of the method, water and aluminum sulfate are introduced by way of transfer method 22 into mixing or reaction vessel 12 to form a first mixture of the preparation mixture 14. The relative amounts of each of these components are adjusted to provide the first mixture so that it has a pH in the range of from 1.5 to 6.5 while also keeping in mind the targeted percent solids of the final slurry mixture of the preparation mixture 14 and the targeted weight percentages of the silica and alumina to be contained in the precipitate solids of the final slurry mixture.

Transfer method 22 provides for introducing the components into mixing or reaction vessel 12 and may be by the use of any suitable means, including conduit means or manual means or conveyor belt means or by any other suitable means for conveying the components and introducing them into mixing or reaction vessel 12. Thus, the line depicting transfer method 22 merely represents the introduction of the various components of the preparation mixture 14 that is formed within mixing or reaction vessel 12.

After introducing the aluminum sulfate to the mixing or reaction vessel 12, sodium aluminate is, thereafter, by way of transfer method 22, added to and mixed with the first mixture of preparation mixture 14 in such an amount as to provide a second mixture of preparation mixture 14 having a pH in the range of from 7.5 to 12 to complete the first pH swing of the method.

In the second pH swing of the method, aluminum sulfate is added to the second mixture of preparation mixture 14 in such an amount as to provide a third mixture of preparation mixture 14 that has a pH in the range of from 1.5 to 6.5 while also keeping in mind the targeted percent solids of the final slurry mixture of preparation mixture 14 and the targeted weight percentages of the silica and alumina to be contained in the precipitate solids of the final slurry mixture. After the formation of the third mixture of preparation mixture 14, sodium silicate is added to the third mixture in such an amount as to provide a fourth mixture of preparation mixture 14 that has a pH in the range of from 7.5 to 10 while also keeping in mind the targeted percent solids of the final slurry mixture of preparation mixture 14 and the targeted weight percentages of the silica and alumina to be contained in the precipitate solids of the final slurry mixture. This completes the second pH swing of the method.

In the third pH swing of the method, aluminum sulfate is added to the fourth mixture to thereby lower the pH of preparation mixture 14 and to thereby form a fifth mixture having a pH in the range of from 1.5 to 6.5 while also keeping in mind the targeted percent solids of the final slurry mixture of preparation mixture 14 and the targeted weight percentages of the silica and alumina to be contained in the precipitate solids of the final slurry mixture. After the formation of the fifth mixture of preparation mixture 14, sodium aluminate is added to the fifth mixture to thereby raise the pH of preparation mixture 14 and to thereby form a sixth mixture having a pH in the range of from 7.5 to 12 while also keeping in mind the targeted percent solids of the final slurry mixture of the preparation mixture 14 and the targeted weight percentages of the silica and alumina to be contained in the precipitate solids of the final slurry mixture. This completes the third pH swing of the method.

In the forth pH swing of the method, aluminum sulfate is added to the sixth mixture to thereby lower the pH of preparation mixture 14 and to thereby form a seventh mixture having a pH in the range of from 1.5 to 6.5 while also keeping in mind the targeted percent solids of the final slurry mixture of preparation mixture 14 and the targeted weight percentages of the silica and alumina to be contained in the precipitate solids of the final slurry mixture. After the formation of the seventh mixture of preparation mixture 14, sodium silicate is then added to the seventh mixture to thereby raise the pH of the preparation mixture 14 and to thereby form an eighth mixture having a pH in the range of from 7.5 to 12 while also keeping in mind the targeted percent solids of the final slurry mixture of the preparation mixture 14 and the targeted weight percentages of the silica and alumina to be contained in the precipitate solids of the final slurry mixture. This completes the forth pH swing of the method.

In one embodiment of the pH swing method, the final slurry from which the precipitate solid is recovered may be from the eighth mixture of preparation mixture 14. Thus, the final slurry of the mixing or reaction vessel 12, which in this case is the eight mixture of preparation mixture 14, is transferred from the mixing or reaction vessel 12 by way of line 24 for further processing in order the recover the precipitate solids. While the further processing steps or equipment are not depicted in FIG. 2, it is noted that the final slurry may be filtered using any of the methods or means known by those skilled in the art as previously noted herein. The filtered precipitate solids may be washed, preferably with water, to remove impurities and spray-dried. The recovered precipitate solids may be dried or calcined, or both.

The following example is presented to further illustrate certain aspects of the invention, but it is not to be construed as limiting the scope of the invention.

EXAMPLE I

The description in this Example I illustrates the inventive pH swing method of preparing the amorphous silica-alumina composition of the invention. Further presented are physical property data concerning the amorphous silica-alumina product made by the pH swing method.

The inventive amorphous silica-alumina powder was prepared using a pH swing precipitation process that included four pH swings conducted in a single, so-called strike tank. In the preparation procedure, a water heel was first added to the empty strike tank. Subsequently, aqueous solutions of aluminum sulfate, sodium alumina, and sodium silicate were added in a sequential manner in the order and relative amounts as presented in Table 1 to the liquor contained in the strike tank to provide the liquor pH as also indicated in Table 1. Four pH swings were performed at a temperature of approximately 55° C. and a constant agitation rate of 43 rpm. The addition and mixing time for each step approximated five minutes. At the end of the last (fourth) pH swing, the solids content of the final liquor, or slurry, was around six weight percent (6 wt %). These solids were recovered and washed. The recovered and washed solids were, again, washed, and, then, spray-dried to form the final amorphous silica-alumina powder.

TABLE 1

Order of the Addition and Amounts of Reaction Components to Strike Tank and the pH of the Resulting Liquor of Each Step

| pH Swing | Step No. | Added Component | Relative Mass of Added Component | pH of Liquor after Addition |
|---|---|---|---|---|
| | 1 | Water heel | 19039 | |
| First pH swing | 2 | Aluminum sulfate | 1777 | 3.2 |
| | 3 | Sodium aluminate | 974 | 8.3 |
| Second pH swing | 4 | Aluminum sulfate | 611 | 4.1 |
| | 5 | Sodium silicate | 1784 | 9.1 |
| Third pH swing | 6 | Aluminum sulfate | 1823 | 3.6 |
| | 7 | Sodium aluminate | 1211 | 9.1 |
| Forth pH swing | 8 | Aluminum sulfate | 600 | 6.5 |
| | 9 | Sodium aluminate | 1802 | 9.6 |

The spay-dried, amorphous silica-alumina powder that had been calcined at 538° C. (1000° F.) was analyzed by Aluminum ($^{27}$Al) Solid-State NMR with magic angle high-speed (14 to 15 kHz) sample spinning. The $^{27}$Al NMR spectrum of the amorphous silica-alumina powder that was determined in accordance with the methodology described earlier herein is presented in FIG. 1. As can be seen from observation of this NMR spectrum, aside from the reference peak, there are three other peaks at locations of approximately 3 ppm, 30 ppm, and 65 ppm of the chemical shift scale. The peak at the 65 ppm location corresponds to tetrahedral aluminum sites in the lattice, the peak at the 30 ppm location corresponds to the penta-coordination aluminum site, and the peak at the 3 ppm location corresponds to the octahedral aluminum site of the spinel structure. The NMR spectrum shows that a significant amount of the aluminum is present in the form of penta-coordinated aluminum as compared to the other forms of aluminum.

Figure 3:
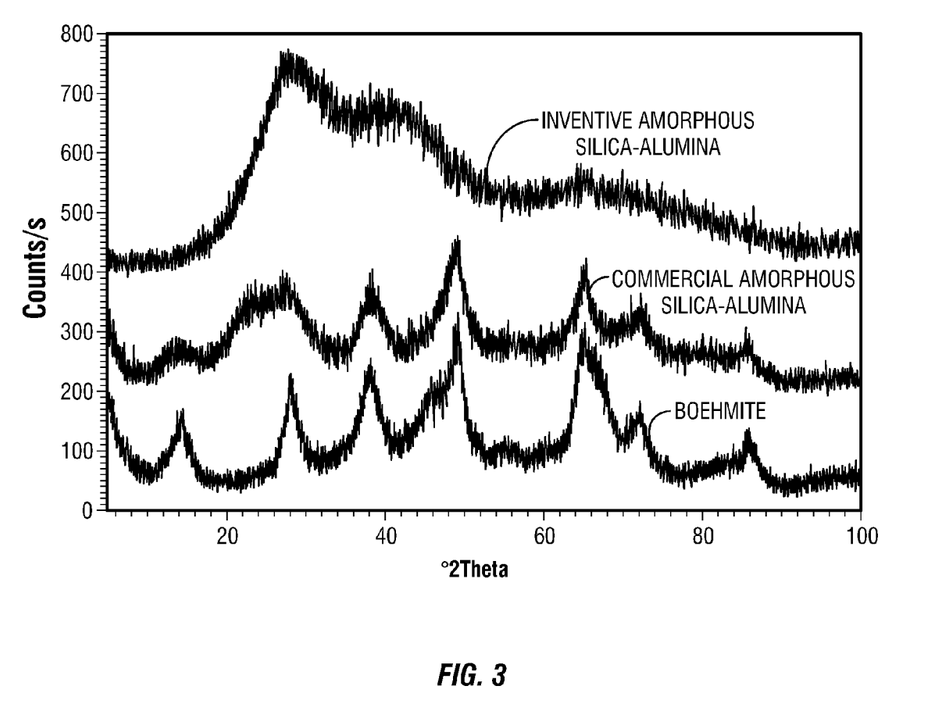
FIG. 3 presents the powder x-ray diffraction spectra of the inventive amorphous silica-alumina powder, a commercially available amorphous silica-alumina powder, and a boehmite powder.

The spray-dried silica-alumina powder and comparison samples of boehmite alumina and a commercial amorphous silica-alumina product used by Criterion Catalyst Company in its manufacture of certain of its hydroprocessing catalysts were each analyzed by the use of a standard powder X-ray diffraction methodology. The spectra of these three compositions are presented in FIG. 3. As may be observed, the XRD spectra of the boehmite and commercial silica-alumina samples show significant crystallinity by having numerous XRD peaks that are representative of crystalline components contained in the compositions. On the other hand, in comparison, the XRD spectrum of silica-alumina powder of the invention shows a presence of very little crystalline material.

That which is claimed is:

1. A method of making a silica-alumina composition, wherein said method comprises:
    (a) combining within a mixing zone water and aluminum sulfate to provide a mixture having a pH in the range of from 1.5 to 6.5;
    (b) thereafter, increasing the pH of said mixture to within the range of from 7.5 to 12 by adding sodium silicate to said mixture within said mixing zone; and
    (c) recovering a precipitate solid from said mixture in said mixing zone, wherein said precipitate solid comprises highly amorphous silica-alumina containing less than 10 weight percent alumina that is in the crystalline phase and having an A/B ratio exceeding 2.2.

2. A method as recited in claim 1, further comprising, prior to recovering step (c):
    (d) after increasing step (b), lowering the pH of said mixture to within the range of from 1.5 to 6.5 by adding aluminum sulfate to said mixture within said mixing zone; and
    (e) thereafter, increasing the pH of said mixture to within the range of from 7.5 to 12 by adding sodium aluminate to said mixture within said mixing zone.

3. A method as recited in claim 2, further comprising:
    (f) after increasing step (e), lowering the pH of said mixture to within the range of from 1.5 to 6.5 by adding aluminum sulfate to said mixture within said mixing zone; and
    (e) thereafter, increasing the pH of said mixture to within the range of from 7.5 to 12 by adding sodium silicate to said mixture within said mixing zone.

4. A method of making a silica-alumina composition, wherein said method comprises:
    forming within a mixing zone a precipitate solid comprising highly amorphous silica-alumina containing less than 10 weight percent alumina that is in the crystalline phase and having an A/B ratio exceeding 2.2 by:
    (a) introducing water into said mixing zone;
    (b) introducing aluminum sulfate into said mixing zone so as to provide a mixture comprising water and aluminum sulfate having a pH in the range of from 1.5 to 6.5;
    (c) thereafter, introducing sodium aluminate into said mixing zone to thereby increase the pH of said mixture to within the range of from 7.5 to 12;
    (d) thereafter, introducing aluminum sulfate into said mixing zone to thereby lower the pH of said mixture to within the range of from 1.5 to 6.5; and
    (e) thereafter, introducing sodium silicate into said mixing zone to thereby increase the pH of said mixture to within the range of from 7.5 to 12; and
    recovering said precipitate solid from said mixture.

5. A method as recited in claim 4, further comprising, prior to the recovering step:
    (f) after step (e), introducing aluminum sulfate into said mixing zone to thereby lower the pH of said mixture to within the range of from 1.5 to 6.5;
    (g) thereafter, introducing sodium aluminate into said mixing zone to thereby increase the pH of said mixture to within the range of from 7.5 to 12;
    (h) thereafter, introducing aluminum sulfate into said mixing zone to thereby lower the pH of said mixture to within the range of from 1.5 to 6.5; and
    (i) thereafter, introducing sodium silicate into said mixing zone to thereby increase the pH of said mixture to within the range of from 7.5 to 12.

6. A method of making an amorphous silica-alumina composition, wherein said method comprises:
    (a) combining water and aluminum sulfate to provide a first mixture having a pH in the range of from 1.5 to 6.5;
    (b) adding sodium aluminate to said first mixture to provide a second mixture having a pH in the range of from 7.5 to 12;
    (c) adding aluminum sulfate to said second mixture to provide a third mixture having a pH in the range of from 1.5 to 6.5;
    (d) adding sodium silicate to said third mixture to provide a forth mixture having a pH in the range of from 7.5 to 12;

(e) adding aluminum sulfate to said forth mixture to provide a fifth mixture having a pH in the range of from 1.5 to 6.5;

(f) adding sodium aluminate to said fifth mixture to provide a sixth mixture having a pH in the range of from 7.5 to 12;

(g) adding aluminum sulfate to said sixth mixture to provide a seventh mixture having a pH in the range of from 1.5 to 6.5;

(h) adding sodium silicate to said seventh mixture to provide an eighth mixture having a pH in the range of from 7.5 to 12; and (i) recovering a precipitate solid from said eighth mixture, wherein said precipitate solid comprises highly amorphous silica-alumina containing less than 10 weight percent alumina that is in the crystalline phase and having an A/B ratio exceeding 2.2.

7. A method as recited in claim 1, further comprising: calcining said precipitate solid in the presence of an oxygen-containing atmosphere at a calcination temperature in the range of from 275° C. to 1000° C.

8. A method as recited in claim 2, further comprising: calcining said precipitate solid in the presence of an oxygen-containing atmosphere at a calcination temperature in the range of from 275° C. to 1000° C.

9. A method as recited in claim 3, further comprising: calcining said precipitate solid in the presence of an oxygen-containing atmosphere at a calcination temperature in the range of from 275° C. to 1000° C.

10. A method as recited in any one of claims 7, 8 or 9, wherein said precipitate solid has a surface area in the range of from 190 m$^2$/g to 400 m$^2$/g.

11. A method as recited in any one of claims 7, 8 or 9, wherein said precipitate solid has a silica content in the range of from 10 to 90 weight percent, with the weight percent being based on the total dry weight of said precipitate solid.

12. A method as recited in claim 4, further comprising: calcining said precipitate solid in the presence of an oxygen-containing atmosphere at a calcination temperature in the range of from 275° C. to 1000° C.

13. A method as recited in claim 5, further comprising: calcining said precipitate solid in the presence of an oxygen-containing atmosphere at a calcination temperature in the range of from 275° C. to 1000° C.

14. A method as recited in claim 12 or 13, wherein said precipitate solid has a surface area in the range of from 190 m$^2$/g to 400 m$^2$/g.

15. A method as recited in claim 12 or 13, wherein said precipitate solid has a silica content in the range of from 10 to 90 weight percent, with the weight percent being based on the total dry weight of said precipitate solid.

16. A method as recited in claim 6, further comprising: calcining said precipitate solid in the presence of an oxygen-containing atmosphere at a calcination temperature in the range of from 275° C. to 1000° C.

17. A method as recited in claim 16, wherein said precipitate solid has a surface area in the range of from 190 m$^2$/g to 400 m$^2$/g.

18. A method as recited in claim 17, wherein said precipitate solid has a silica content in the range of from 10 to 90 weight percent, with the weight percent being based on the total dry weight of said precipitate solid.

\* \* \* \* \*